United States Patent [19]
Parker

[11] 3,990,795
[45] Nov. 9, 1976

[54] APPARATUS FOR MONITORING SUSPENDED PARTICLES IN A LIQUID

[75] Inventor: Adrian Roger Parker, St. Austell, England

[73] Assignee: Partech (Electronics) Limited, Welwyn Garden City, England

[22] Filed: Oct. 4, 1974

[21] Appl. No.: 512,298

[30] Foreign Application Priority Data
Oct. 8, 1973 United Kingdom............... 46912/73

[52] U.S. Cl................................ 356/103; 250/574; 356/208
[51] Int. Cl.²......................................... G01N 21/06
[58] Field of Search .......... 250/573, 574, 576, 577; 356/103, 201, 208, 210

[56] References Cited
UNITED STATES PATENTS
2,215,211  9/1940  Devol................................. 250/237
3,691,391  9/1972  Kishi................................... 356/208

FOREIGN PATENTS OR APPLICATIONS
743,330  9/1966  Canada............................... 356/103

Primary Examiner—John K. Corbin
Assistant Examiner—Richard A. Rosenberger
Attorney, Agent, or Firm—Cushman, Darby & Cushman

[57] ABSTRACT

A turbidity measuring instrument has a chamber through which liquid to be examined flows, the chamber having a constant head inlet and a weir overflow outlet so that a static liquid level is maintained in the chamber, light being directed vertically into the liquid from above and back-scattered light from particles suspended in the liquid being measured photoelectrically by a detector head located in a sealed housing with a light source above the liquid level.

3 Claims, 1 Drawing Figure

U.S. Patent  Nov. 9, 1976  3,990,795
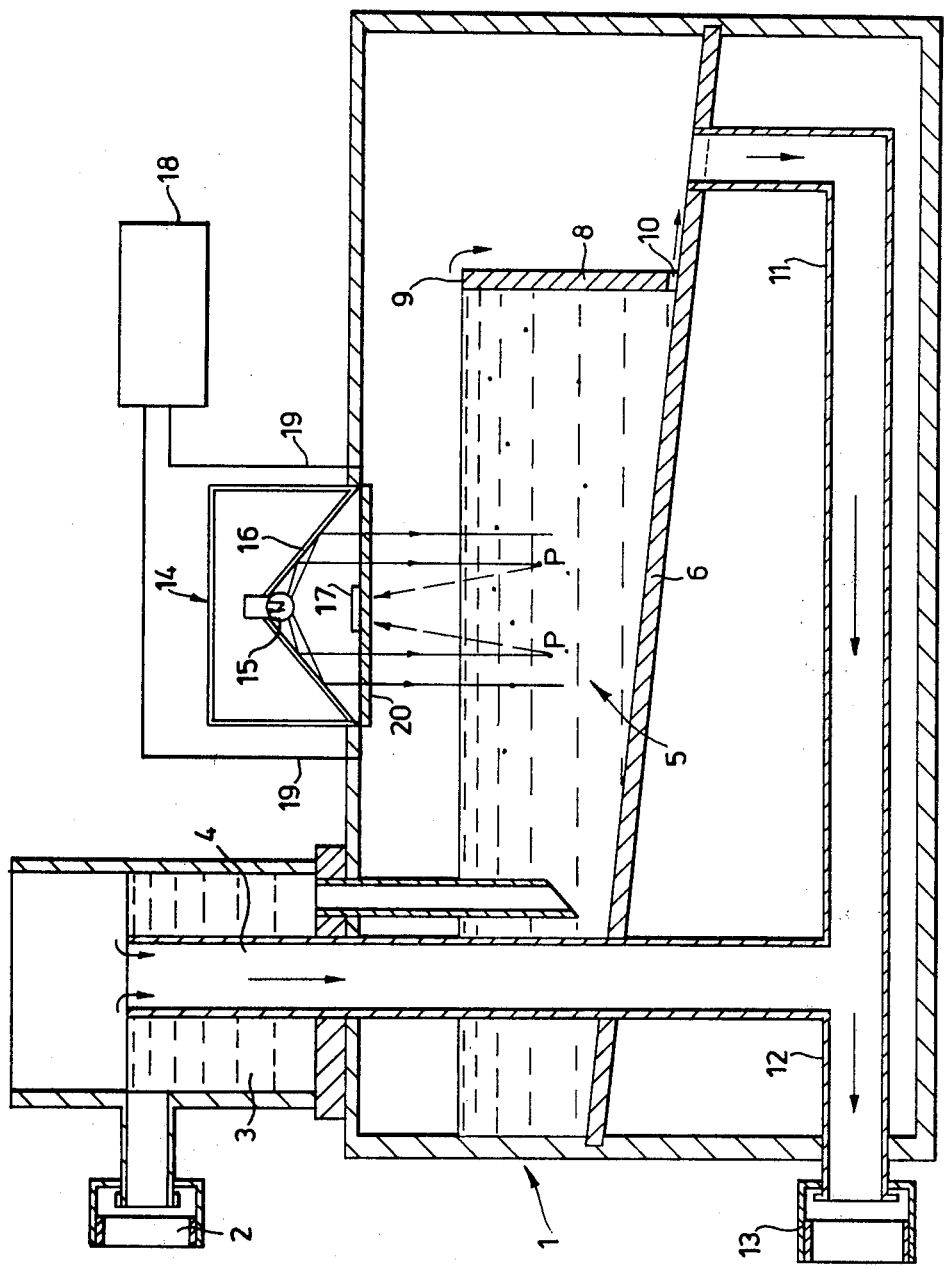

APPARATUS FOR MONITORING SUSPENDED PARTICLES IN A LIQUID

This invention relates to apparatus for monitoring the presence of suspended particles in a liquid, for example with a view to measuring the quantity of suspended particles in a liquid.

An object of the invention is to provide apparatus for use in detecting and monitoring the presence of suspended particles in a liquid by making use of the light-scattering properties of such particles.

According to the invention there is provided apparatus for monitoring the presence of suspended particles in a liquid, comprising a chamber having an inlet at one end for a liquid to be monitored, and a wall at the opposite end having a horizontal upper edge which forms a weir over which the liquid flows to maintain a constant liquid level in the chamber, a housing located above the chamber, a light source mounted in the housing and arranged to direct a light beam downwardly into the liquid in the chamber, and a photoelectric detector mounted in the housing to detect light scattered in an upward direction from suspended particles in the liquid flowing through the chamber.

An important advantage of the apparatus according to the invention is that the light source and the photoelectric detector are contained in a housing which does not come into contact with the liquid under examination and which, therefore, is not prone to contamination by the liquid.

Since the detector and the light source are arranged in the same housing, the detector responds effectively to back-scattered light from the suspended particles in the liquid.

Preferably the light source housing includes a reflector arranged to direct light from the source into a downwardly directed beam.

The detector is preferably arranged centrally of the housing directly below the light source.

In a preferred embodiment the inlet is connected to an inlet chamber having an overflow outlet arranged so as to maintain a constant head of liquid relative to the said inlet. This arrangement ensures that the rate of flow of liquid under examination through the chamber is maintained substantially constant.

The overflow outlet from the inlet chamber and the overflow from the weir are preferably connected to a common outlet pipe.

The photoelectric detector may be connected to any suitable form of electronic analyser according to the measurements to be made on the suspended particles detected by the apparatus. Such an analyser will include means to discriminate between light scattered from the particles suspended in the liquid and light reflected from the surface of the liquid or from the bottom of the chamber containing the liquid. The minimise the amount of light entering the photoelectric detector after reflection from the bottom of the chamber the chamber is preferably provided with a floor which is inclined to the horizontal.

A practical embodiment of the invention will now be described, merely by way of example, with reference to the accompanying drawing, which is a diagrammatic sectional view of an apparatus according to one embodiment of the invention.

Referring to the drawing, the apparatus illustrated is intended to monitor the presence of suspended particles in a liquid, and to measure the suspended particle content or turbidity of the liquid. The liquid under examination may, for example, comprise drinking water, starch or beer, or any liquid in which the suspended particle content has to be monitored continuously.

The apparatus has a box-like casing 1 provided with an inlet 2 for the liquid to be monitored, the inlet 2 leading into an inlet chamber 3 which is provided with a vertical overflow outlet pipe 4 arranged within the chamber 3 so that a substantially constant head of liquid is maintained in the inlet chamber 3 despite fluctuations in the supply pressure of the liquid.

The inlet chamber 3 is arranged directly above a flow chamber 5 having a sloping floor 6, the inlet chamber 3 communicating with the shallower, upstream, end of the flow chamber 5 through a downwardly extending inlet pipe 7 which has an open end near the floor 6. The end of the flow chamber 5 remote from the inlet pipe 7 is delimited by a vertical wall 8 having a horizontal upper edge 9 which defines a weir over which liquid flows after passing through the flow chamber 5. A number of outlet openings 10 are provided at the base of the vertical wall 8 adjacent the floor 6, to permit a small outlet flow of liquid and prevent the accumulation of sediment on the floor 6. After flowing over the weir and through the openings 10 the liquid enters an overflow collection pipe 11, as illustrated diagrammatically by arrows in FIG. 1.

The overflow outlet pipe 4 from the inlet chamber 3 and the overflow collection pipe 11 are connected to a common outlet pipe 12 which leads to an outlet 13 disposed on the outside of the casing 1.

The arrangement of the apparatus is such that when the inlet 2 is connected to a source of liquid to be monitored the liquid flows at a substantially constant rate through the flow chamber 5, in which the liquid is examined optically for suspended particles.

To perform the optical analysis of the particle-containing liquid a housing 14 is mounted in the upper wall of the casing 1 directly above the flow chamber 5, between the inlet pipe 7 and the weir. The housing 14 contains a point source of light 15 mounted at a focal point of a conical or paraboloidal reflector 16 arranged to direct light from the source 15 into a vertically downwardly directed substantially parallel beam, as illustrated in the drawing. The vertical light beam from the source 15 enters the liquid flowing through the flow chamber 5 in a vertical direction and is scattered by suspended particles P contained in the liquid, as shown diagrammatically. A proportion of the light scattered backwardly by the suspended particles passes in an upward direction out of the liquid and is detected by a photoelectric detector 17 arranged in the centre of the housing 14 directly beneath the light source 15.

The photoelectric detector 17 is connected to an electronic analyser 18 of a known type, which provides an indication of the quantity of light-scattering particles in the liquid under examination and therefore of the turbidity of the liquid. The analyser 18 is arranged to discriminate between light entering the photoelectric detector 17 as a result of reflection at the surface of the liquid or reflection at the floor 6 of the chamber, so as to provide a quantitative measurement of turbidity. For example, the analyser 18 may be calibrated by measurement of light entering by the photoelectric detector 17 when clear liquid such as distilled water flows through the chamber 5. Electrical leads 19 connecting the photocell 17 to the analyser 18 extend along the upper surface of a glass cover plate 20 which seals the bottom of the reflector 16, the photocell 17 being mounted on the upper surface of the cover plate 20, so that all the optical and photoelectric components are effectively sealed.

I claim:

1. Apparatus for monitoring the presence of suspended particles in a liquid, comprising:

means defining an examination chamber, inlet means at one end of the chamber for a liquid to be monitored, a wall defining a weir at the opposite end of the chamber, the examination chamber having a floor which is inclined to the horizontal, the weir defining a constant liquid level in the chamber in use of the apparatus, a housing located above the examination chamber and above the liquid level therein, a light source mounted in the housing, reflector means for directing a light beam from the source vertically downwardly in parallel rays for normal incidence into liquid flowing through the chamber to effectively prevent liquid surface reflection, and photoelectric detector means liquid-protectively mounted inside the housing directly vertically below the light source for detecting back-scattered light scattered in an inwardly upward direction from suspended particles illuminated by the beam in said liquid flowing through the chamber, the inclination of said floor being such that any of said light rays reflected normal to said floor is outside the field of view of said photoelectric detector means.

2. The apparatus defined in claim 1 wherein the inlet means comprise an inlet chamber and an inlet conduit leading from the inlet chamber to the examination chamber, the inlet chamber having an overflow outlet arranged so as to maintain a constant head of liquid in said inlet chamber.

3. The apparatus defined in claim 2, including a weir overflow conduit arranged to receive the overflow from the weir, and a common outlet pipe connected to said inlet chamber overflow outlet and to said weir overflow conduit.

* * * * *